United States Patent [19]

Smith et al.

[11] Patent Number: 5,627,033

[45] Date of Patent: May 6, 1997

[54] MAMMALIAN EXPRESSION VECTORS

[75] Inventors: John M. Smith, Columbia Heights; John E. Humphrey, Maple Grove; Monica L. Tsang; James A. Weatherbee, both of North Oaks, all of Minn.

[73] Assignee: Research & Diagnostics Systems, Inc., Minneapolis, Minn.

[21] Appl. No.: 411,490

[22] Filed: Mar. 28, 1995

[51] Int. Cl.$^6$ ................................................. C12Q 1/68
[52] U.S. Cl. ................ 435/6; 435/91.41; 435/172.3; 435/320.1; 435/325; 435/358; 435/365
[58] Field of Search .................. 435/6, 172.3, 91.1, 435/320.1, 91.41

[56] References Cited

U.S. PATENT DOCUMENTS

| | | | |
|---|---|---|---|
| 5,149,636 | 9/1992 | Axel et al. | 435/69.1 |
| 5,266,683 | 11/1993 | Oppermann et al. | 530/326 |

FOREIGN PATENT DOCUMENTS

| | | | |
|---|---|---|---|
| 62011096 | 1/1987 | Japan | C12N 15/00 |
| 04179485 | 6/1992 | Japan | C12N 15/65 |

OTHER PUBLICATIONS

R.J. Kaufman, "Selection and Coamplification of Heterologous Genes in Mammalian Cells", in *Methods in Enzymology*, 185:537–566 (1990).

R.J. Kaufman, "Vectors Used for Expression in Mammalian Cells" in *Methods in Enzymology*, 185:487–511 (1990).

Kim et al., (Abstract) "Effects of Multiple Mutations at the Conserved TATA Sequence of Bacteriophage SP6 Promoter on Transcription Activity", *Biochem. and Mol. Biol. Int.* 31(1):153–9 (1993).

Mulligan and Berg (Proc. Natl. Acad. Sci., 78:2072–2076 (1981)).

Pauly, et al., "The Initiation of Accuracy of the SV40 Early Transcription is Determined by the Functional Domains of Two TATA elements", *Nucleic Acids Res.*, 20(5):975–982 (1992).

"Expression of Proteins" Chapter 16, Expression of Cloned Genes in Cultured Mammalian Cells, in *Molecular Cloning: A Laboratory Manual*, J. Sambrook ed, 2nd ed., pp. 16.3–16.31 (1989).

Japanese Publ. No. 04–179485 (Abstract) DIALOG File 347 (JAPIO).

WPI Acc. No. 92–263665/32 (Abstract) DIALOG File 351 (Derwent WPI).

Niwa et al., "Efficient Selection for High–expression Transfectants with a Novel Eukaryotic Vector", *Gene* 108:193–199 (1991).

*Primary Examiner*—James Ketter
*Attorney, Agent, or Firm*—Fredrickson & Byron, P.A.

[57] ABSTRACT

A vector system that allows the rapid and effective screening of recombinant constructs. The vector system includes a marker protein useful for identifying transfected cell lines, wherein the promoter used to express the marker protein has be substantially weakened in comparison to its corresponding wild type form.

29 Claims, No Drawings

MAMMALIAN EXPRESSION VECTORS

TECHNICAL FIELD

The present invention relates to the field of gene expression in mammalian cell systems, and in particular to promoter regions and selector or marker means useful in the development of such systems.

BACKGROUND OF THE INVENTION

The 1980's and 1990's have witnessed a burgeoning science in the area of recombinant DNA. Recombinant DNA processes involve the identification and isolation of desired gene sequences from natural sources. Various methods and biochemical tools have been developed in order to specifically incorporate such sequences into in vitro expression systems. Such systems are intended to produce large amounts of the protein product coded for by the gene sequences.

Expression of such genes in bacterial expression systems is widely used for research applications, but suffers from a number of drawbacks when applied to the production of gene products such as therapeutic proteins. In particular, it has been found that the protein product of bacterial expression systems does not undergo certain biochemical modifications thought to be necessary for activity of the product as a therapeutic agent. As a result, numerous efforts have been directed at the development of mammalian expression systems. It is generally thought that such expression systems are more likely to result in protein products suitably modified for mammalian use.

Expression in either bacterial (procaryotic) or mammalian (eucaryotic) systems typically involves the incorporation of the gene of choice into a vector, e.g., a plasmid. The vector, or expression construct as it is often referred, is then introduced into a host cell in such a manner as to enable the host cell to transcribe the gene of choice and thereby produce protein. High level expression is typically a prime concern in developing such systems. See generally, pages 16.3–16.28 "Expression of Proteins" in Chapter 16, "Expression of Cloned Genes in Cultured Mammalian Cells, in *Molecular Cloning—Laboratory Manual*, J. Sambrook ed, 2nd ed. (1989).

Transcriptional control regions occur throughout eucaryotic genes. Such genes can, in fact, be divided into three classes on the basis of the specific RNA polymerase that transcribes them into RNA. In particular, specific nucleotides that flank the gene coding region are common among expression systems. A common sequence, likely to be important for proper transcription by RNA polymerase II, is known as the "TATA" box, which occurs about 30 bp from the transcriptional start site. Other conserved sequences have been found roughly 50 to 100 base pairs ("bp") upstream of the start site, among them being a GC-rich sequence and the sequence CCAAT. These sequences provide the recognition sites for specific proteins that serve as transcription factors.

A typical mammalian expression construct consists of a complimentary DNA sequence (otherwise known as a "cDNA" or mini-gene) functionally linked to a promoter region and to a polyA signal. A promoter region is a nucleotide segment that is recognized by a RNA polymerase molecule, in order to begin RNA synthesis (i.e., transcription). In the initiation step the two chains of the nucleic acid double helix come apart, with only one of the two strands at any start site being copied into its RNA complement. The promoter region is itself derived from a viral or mammalian source (constitutive or inducible). These elements are analogous to those necessary for propagation in bacteria. Most mammalian expression constructs also contain a gene useful for selection in mammalian cells.

Ideally, the selection gene is capable of being transformed with the cDNA in order to provide an easily detectable protein product. The presence of the detectable protein product is used to identify transfected cells that have successfully incorporated the construct. The selectable gene is commonly of bacterial origin and is itself usually flanked by a constitutive mammalian promoter and polyA signal. The promoter driving the selectable marker is often of the same type as the promoter used to express the cDNA. This is desirable since vigorous expression of the selectable gene is considered necessary to establish permanent cell lines. See, for instance, R. J. Kaufman, "Selection and Coamplification of Heterologous Genes in Mammalian Cells", in *Methods in Enzymology*, 185:537–566 (1990).

Gene expression in eucaryotic systems carries its own unique attributes and considerations. In prokaryotes, mixing purified RNA polymerase with a template having a promoter region and the necessary reagents and buffers is generally sufficient to obtain specific gene transcription.

Purified eucaryotic RNA polymerase, however, initiates transcription very poorly in vitro, by a process that is essentially random. It is believed that a multiprotein transcription complex is assembled in eucaryotic systems, in order to enable the polymerase to bind to a promoter. The assembly includes both gene-specific and general factors. An example of a general factor is a protein called TFIID, which binds to the above-described "TATA" sequence, common to many promoters.

Expression of recombinant genes in mammalian cells is typically performed in one of two ways. The first approach involves the temporary introduction of DNA into a host cell, under conditions in which the protein is transiently expressed on a short term basis. A common example is the infection of COS cells with simian vacuolating virus 40 ("SV40")based vectors, where the SV40 origin of replication produces manifold copies of the expression vector. A selectable gene is not considered necessary for transient expression.

A second approach to mammalian expression involves the establishment of a permanent mammalian cell line by the stable integration of an expression construct, usually at random, in the host cell genome. The cell line most often used in the past for stable expression has been the Chinese Hamster Ovary ("CHO") cell line, which is a fibroblast-derived cell line. The expression levels for stable CHO cell lines derived from a single transfection can vary from undetectable levels to levels as high as 0.05 micrograms/ml and more. The variation between cell lines is largely a factor of the respective insertion sites for the construct, and/or position effects.

A number of factors can influence the expression of cDNA constructs in stable cell lines. Among the more important factors appears to be the location, i.e., site of insertion, of the construct within the host cell genome. Expression variability that results from the different insertion sites is often referred to as the "position effect". The integration techniques commonly employed result in random positioning, meaning that position effects can be detected but not controlled or predicted.

In this second approach, the expression of lines providing detectable expression levels can be increased further by a process known as gene amplification. Such a process involves the stepwise selection for growth of cultured cells in the presence of increasing concentrations of a substance toxic to the cells. The toxic substance, in turn, can only be inactivated by a corresponding increase in the expression of a gene product that is co-transfected with the expression construct. (R. J. Kaufman, *Methods in Enzymology*, 185:537–566 (1990)).

A long time course is typically associated with the use of such an amplification process. The time course is lengthened even further by virtue of the relatively slow growth rate of CHO cells and by the need to isolate clonal cell lines at each step. As a result, the characterization of different variants is a long and tedious process, often taking six to nine months. Using CHO cells, for instance, the entire process can often require on the order of up to one year or more to achieve optimized levels.

Integration of a construct into a chromosomal site that is transcriptionally active, together with the use of a strong promoter, can often produce cell lines having expression levels that are comparable to those achieved by the amplification of a low expression cell line. Oftentimes the additional screening necessary to identify clones having natural high expression is so laborious, that amplification of a lower expression cell line is preferred.

It is presently quite difficult to specifically and reproducibly integrate a construct into a transcriptionally active site. It is for this reason that research to date has generally focused on the search for stronger promoters. The strength of the promoter used in the expression of the cDNA is considered one of the more important aspects of mammalian expression.

"Strength", in this respect, refers to the ability of the promoter to activate high level expression of its respective gene in a particular system. Some of the earliest promoters characterized for mammalian expression were of viral origin, e.g., SV40 (early and late promoters), the adenovirus major late promoter, the Rous Sarcoma Virus ("RSV") promoter, Cytomegalovirus ("CMV") immediate-early promoter, and the Major-intermediate-early ("MIE") promoters.

As described above, the process of identifying transfected cells has been fostered by the development of selectable markers that are capable of being co-transfected with the gene of interest. Selectable markers commonly employed for the establishment of stable cell lines include various mammalian genes (such as dhfr), as well as bacterial genes, e.g., Neo (G418 resistance), and the *E. coli* gpt gene, driven by a mammalian promoter. (See Kaufman, above).

A mammalian cell typically obtains its supply of GMP, which is a necessary purine nucleotide, either by de novo synthesis from IMP or by salvaging guanine from the culture medium. Guanine salvage can be blocked by using cells that lack hypoxanthine-guanine phosphoribosyltransferase (HPRT), leaving synthesis as the only pathway. Mycophenolic acid, when present in the growth medium, blocks the natural conversion of IMP into XMP, by inhibiting IMP dehydrogenase, and therefore inhibits the de novo synthesis of GMP.

The gpt (guanine phosphoribosyl transferase) gene can be used for selection in the presence of mycophenolic acid ("MPA"). The use of the gpt gene as a selectable marker in mammalian cells was first developed by Mulligan and Berg (Proc. Natl. Acad. Sci., 78:2072–2076 (1981)). The gpt gene can be used as a dominant selection system that can be applied to any type of HPRT (negative) cell.

In use, only cells expressing the *E. coli* gpt gene are able to use xanthine to make XMP and the GMP, and cells that do not express gpt do not survive. Vectors expressing gpt, when integrated into the genome, are therefore able to provide wild-type mammalian cells with the ability to grow in medium containing adenine, xanthine, and the inhibitor mycophenolic acid. The selection can be made more efficient by the addition of aminopterin, which blocks the endogenous pathway of purine biosynthesis. (See, for instance, M. Pauly, et al., *Nucleic Acids Research*, 20:975–982 (1992)).

An optional route to the use of selectable genes such as gpt, is to incorporate antibiotic resistance into the transfected cells. Resistance, however, usually shows a threshold effect, in that a minimal concentration is needed to inhibit wild type cells. Varying levels of antibiotic might also affect the plating efficiency of each cell line as the minimal or maximum levels are approached. The advantage of the gpt selection is that adjustment of the mycophenolic acid concentration is not necessary for different selectable markers and promoters.

Most of the efforts that have been aimed at improving expression levels have therefore focused on increasing the strength of the promoter and/or on gene amplification schemes. Other approaches to circumventing position effects have involved the creation of dicistronic vectors where the selectable marker is positioned as the second gene and is inefficiently translated. See generally, R. J. Kaufman, "Vectors Used or Expression in Mammalian Cells" in *Methods in Enzymology*, 185:487–511 (1990).

Although present techniques for evaluating and optimizing expression levels are useful, to this day they largely remain time consuming, laborious, expensive and unpredictable. It would be highly desirable to have a system for generating and screening constructs in a manner that provides an improved combination of such aspects as time, labor and cost.

SUMMARY OF THE INVENTION

The present invention provides a vector system that allows the rapid and effective screening of recombinant constructs in a manner that provides an optimal combination of such properties as yield, efficiency, time, and cost. In particular, the vector of the present invention provides an improved combination of expression levels and the time required for strain isolation.

As described above, the present use of CHO cells can require up to one year or longer to achieve optimized levels. In contrast, expression systems of the present invention can reach a similar point in a significantly less time, e.g., 6 to 8 weeks or less. Stated differently, a procedure that would entail screening on the order of 1000 clones using conventional techniques can be accomplished by screening on the order of only 100 clones by use of the presently claimed invention. This improvement is made possible by virtue of the higher expression levels detectable using the vector and methods presently described, and leads to a significant savings in time and effort.

In a preferred embodiment, the invention provides a vector useful for selection and expression of a cDNA gene sequence in a mammalian cell system, the vector comprising;

a) a cDNA structural gene sequence encoding a protein product of choice;

b) a cDNA promoter sequence controlling the cDNA sequence;

c) a marker protein sequence encoding a detectable protein product; and d) a marker promoter sequence controlling the marker protein sequence;

wherein the cDNA and marker promoter sequences are cotransformed, and the marker sequence promoter is mutated so as to exhibit an activity level substantially below that of its corresponding wild type.

In a particularly preferred embodiment the marker sequence promoter is an SV40 promoter that has been stably and genetically mutated in order to substantially weaken the promoter activity as compared to the non-mutated, native form. A preferred mutated marker sequence promoter includes the group consisting of double and single transvertional point mutations covering the T+A rich region of the SV 40 early promoter and replication origin. Particularly preferred within this group are mutations located within a domain extending from position 16 to 21, which have been shown to drastically decrease transcription initiation from the early-early start site (EES1) as compared to its corresponding "wild type" (pSEG A0).

Such a weakened promoter will occasionally be referred to herein as a "knockdown" promoter, to described the situation in which a wild type, higher activity, promoter has been genetically altered at or near its functional domain to achieve a substantially lower activity level. In a preferred embodiment, a weakened SV40 promoter is used in mouse myeloma cell lines, in conjunction with the marker protein sequence that encodes for a mycophenolic/gpt selection scheme.

In another aspect the invention provides an expression system comprising a mammalian cell line transfected with a vector as described herein, wherein the vector allows the rapid identification and selection of suitable cell lines expressing the cDNA sequence. Preferred expression systems employ a vector comprising a weakened early SV40 promoter in combination with a gene that encodes for a mycophenolic/gpt selection scheme, and a cell line selected from a mouse myeloma cell line, e.g., either an NSO or NS-1 cell line.

A particularly preferred embodiment of the present invention provides a vector that comprises the EcoRI-PstI fragment from the plasmid pSV2gpt, the fragment comprising (in order from the EcoRI site): the beta-lactamase gene for ampicillin resistance in *E. coli*; an origin of replication for growth of the plasmid in *E. coli*; the SV 40 early promoter with the A-series mutation number 7 as described by Pauly, et al., the *E. coli* gpt gene for the MPA selection; and the SV40 polyA region bounded by the PstI site.

The PstI site is preferably followed by the SRα296 promoter for cDNA expression, but any constitutive or inducible promoter (e.g., CMV) can be included. The promoter for cDNA expression is followed by a cloning site for cDNA insertion which is then followed by a polyA sequence for cDNA/mRNA stability. Finally, after the poly A region, the immnoglobulin heavy chain enhancer is included as a 2.5 kb genomic DNA fragment.

In yet another aspect, the invention provides a method that comprises the steps of constructing a vector comprising a cDNA sequence, a controlling cDNA promoter sequence that functions at a pre-determined activity level, a marker sequence, and a weakened marker sequence promoter that functions at an activity level substantially below that of its corresponding wild type.

The invention further provides a method of using a vector of the type described herein, the method comprising the steps of transfecting a mammalian cell population with a vector that comprises a cDNA sequence, a controlling cDNA promoter sequence, a marker sequence, and a controlling marker sequence promoter that functions at an activity level substantially below that of its corresponding wild type, and (b) selecting for cell lines expressing high levels of protein product by selecting for the marker protein.

DETAILED DESCRIPTION

The present invention provides a vector system that allows the rapid and effective screening of recombinant constructs by the use of a novel vector. The vector comprises;

a) a cDNA structural gene sequence encoding a protein product of choice;

b) a cDNA promoter sequence controlling the cDNA sequence;

c) a marker protein sequence encoding a detectable protein product; and d) a marker promoter sequence controlling the marker protein sequence;

wherein the cDNA and marker promoter sequences are cotransformed, and the marker sequence promoter has been weakened in order to function at an activity level substantially below that of its corresponding wild type.

Not intending to be bound by theory, it is believed that the weakened promoter activity associated with the marker sequence allows the rapid identification and isolation of cell lines. This is particularly true in cells where the vector (and in turn cDNA region) have been incorporated into regions of particularly high transcriptional activity. It is believed that the high rate of transcription is able to compensate for the weakened marker promoter activity, in order to provide detectable levels of the marker.

The cDNA promoter, in turn, continues to function at a relatively high rate of expression, particularly in comparison to the marker promoter activity. In view of the disparity between the activity of cDNA and marker promoter regions, the high rate of transcriptional activity necessary to identify the marker expression will correspond with a high rate of transcription of the cDNA region.

Any suitable cDNA sequence can be used in a vector of the present invention. cDNA sequences suitable for use in the present invention include those commonly employed in recombinant processes. Typically such sequences encode protein products having particular use, such as for therapeutic or diagnostic purposes. Such cDNA can be identified and isolated in a variety of ways known to those skilled in the art. See generally, pages 16.3–16.28 "Expression of Proteins" in Chapter 16, "Expression of Cloned Genes in Cultured Mammalian Cells, in *Molecular Cloning—Laboratory Manual*, J. Sambrook ed, 2nd ed. (1989).

Examples of cDNA sequences of present commercial interest include those for the following protein products and their corresponding receptors:

| Product | Conventional Expression System |
|---|---|
| Immunomodulators: | |
| Interferon-α | *E. coli*, yeast |
| Interferon-beta | Mouse cells, CHO, mammalian cells |
| Interferon-gamma | *E. coli*, yeast, CHO, mammalian cells |
| IL-1 | *E. coli*, yeast, surface adherent cells |
| IL-2 | *E. coli*, yeast, surface adherent cells, P. |
| IL-3 | *E. coli*, yeast, CHO |
| IL-6 | *E. coli* |

-continued

| Product | Conventional Expression System |
|---|---|
| TNF | E. coli, yeast, P. pastoris |
| TNF-beta | E. coli |
| Growth Factors: | |
| G-CSF | E. coli, yeast, CHO |
| M-CSF | E. coli, yeast, CHO |
| GM-CSF | E. coli, yeast, CHO |
| Fibroblast growth factor | E. coli, yeast, animal cells |
| TGF-α | E. coli, yeast |
| TGF-beta | Yeast |
| Epidermal growth factor | E. coli, yeast, animal cells |
| Platelet-derived growth factor | E. coli, yeast, surface adherent cells |
| Connective tissue activator peptide | E. coli |
| Angiogenin differentiation-inducing factor | Surface adherent cells |
| Fibronectin | Yeast |
| EPO | Surface adherent cells, CHO |
| Hormones: | |
| Insulin-like growth factor 1 | E. coli, yeast, P. pastoris |
| Insulin-like growth factor 2 | E. coli, yeast |
| Human growth hormone | E. coli, yeast, CHO, surface adherent cells, transgenic mice |
| hGH releasing factor | E. coli, yeast |
| Somatostatin | E. coli |
| Calcitonin | E. coli, yeast |
| Human chorionic gonadotrophin | Yeast, murine cells |
| Luteinizing hormone | Murine cells |
| Relaxin | E. coli |
| Insulin | E. coli, yeast |
| Proinsulin | E. coli, yeast |
| Beta-endorphin | E. coli |
| Blood Proteins: | |
| Human serum albumin | E. coli, yeast, potato, tomato, P. pastoris, H. polymorphia, K. lactis |
| Hemoglobin | E. coli, yeast, transgenic mice and pigs |
| Antithrombin III | CHO |
| Factor VII | BHK, yeast |
| Factor VIII | Surface adherent cells, CHO, S. prombe |
| Factor IX | BHK, transgenic sheep |
| Factor XIII | E. coli, yeast |
| von Willebrand factor | Surface adherent cells |
| t-PA | E. coli, yeast, CHO, transgenic mice |
| Urokinase | Surface adherent cells |
| Prourokinase | E. coli, surface adherent cells |
| Streptokinase | P. pastoris |
| Hirudin | Yeast, H. polymorpha |
| Protein C | Surface adherent cells |
| Thrombomudulin | Mammalian cells |
| Alpha-1-antitrypsin | E. coli, yeast, transgenic sheep |
| Apolipoprotein A-1 | E. coli |
| Apolipoprotein A-IV | E. coli |
| Apolipoprotein E | E. coli |
| Atrial natriuretic factor | E. coli |
| Platelet factor 4 | E. coli |
| Inhibitors: | |
| Mullerian inhibiting substance | CHO |
| Elastase inhibitor | E. coli |
| Lipocortin | E. coli |
| Enzymes: | |
| Lysozyme | E. coli, yeast |
| SOD | E. coli, yeast, surface adherent cells, P. pastoris |
| Renin | E. coli, CHO |

-continued

| Product | Conventional Expression System |
|---|---|
| Gastric lipase protein | Yeast |
| Vaccines: | |
| Hepatitis B | CHO, yeast, P. pastoris, H. polymorpha |
| Whooping cough | E. coli |
| Malaria | Yeast |

Promoters useful as cDNA promoters in the present invention include those commonly employed for recombinant applications. Those skilled in the an will appreciate the manner in which cDNA promoters can be identified and incorporated into an expression vector in order to realize and optimize their intended function. The "activity" of the cDNA promoter, as referred to herein, should preferably be at a level that allows the cDNA to be transcribed at a substantially higher rate than the corresponding rate of transcription associated with the marker protein. Preferably, the promoter used for cDNA expression in a particular vector is the wild type, or other suitably active form, of the same type of promoter that has been weakened and used for expression of the associated marker protein.

Marker proteins useful in the present invention include those that provide detectable, non-interfering protein products, the corresponding genes for which are capable of cotransformation with the cDNA of interest. Suitable marker proteins are those that are necessary for growth of the respective cell line. Marker proteins known as "dhfr" (dihydrofolate reductase); "add" (adenosine deaminase); and "CS" (glutamine synthetase), are particularly useful, due in part to the need for subsequent amplification in most selection and expression processes. Salvage enzymes of the nucleotide biosynthetic pathways are also useful, since many of those pathways are easily inhibited.

Those skilled in the art, given the present specification, would be able to choose from among the following selection means and associated marker proteins:

| Selection means | Marker protein/gene |
|---|---|
| Methotrexate | Dihydrofolate reductase |
| Cadmium | Metallothionein |
| PALA | CAD |
| Xyl-A-or adenosine and 2'-deoxycoformycin | Adenosine deaminase |
| Adenine, azaserine, and coformycin | Adenylate deaminase |
| 6-Azauridine, pyrazofuran | UMP Synthetase |
| Mycophenolic acid with limiting xanthine | Xanthine-guanine phosphoribosyltransferase |
| Hypoxanthine, aminopterin, and thymidine (HAT) | Mutant HGPRTase or mutant thymidine kinase |
| 5-Fluorodeoxyuridine | Thymidylate synthetase |
| Multiple drugs | P-glycoprotein 170 |
| Aphidicolin | Ribonucleotide reductase |
| Methionine sulfoximine | Glutamine synthetase |
| β-Aspartyl hydroxamate or Albizziin | Asparagine synthetase |
| Canavanine | Arginosuccinate synthetase |
| α-Difluromethylornithine | Ornithine decarboxylase |
| Compactin | HMG-CoA reductase |
| Tunicamycin | N-Acetylglucosaminyl transferase |
| Borrelidin | Threonyl-tRNA synthetase |
| Ouabain | Na+, K+-ATPase |

Native promoters useful for the expression of marker sequences can be weakened by any suitable means. A preferred promoter is one that provides a useful, but not excessive amount of expression in the wild type state. It has been found, for instance, that the transcriptional activity of the SV40 promoter expressing the gpt marker gene described herein can be weakened by altering its RNA polymerase binding site. The characterization of numerous mutations and their effect on the transcriptional activity of the SV40 early promoter has been reported. Pauly, M. et al., *Nucleic Acids Research* 20:975–982 (1992), the disclosure of which is incorporated herein by reference.

Examples of suitable wild type marker promoters include those of viral origin, e.g., SV40 (early and late promoters), the adenovirus major late promoter, the Rous Sarcoma Virus ("RSV") promoter, Cytomegalovirus ("CMV") immediate-early promoter, and the Major-intermediate-early ("MIE") promoters. These promoters are attractive because of their strength, constitutive expression and the ability to be expressed in varied cell lines.

Any mutation that sufficiently decreases the rate of transcription initiation can also serve to weaken a promoter for purposes of the present invention. The TATA sequence alteration is believed to a very reliable site for mutation, and is therefore preferred, since the ability to selectively mutate the TATA region is within the skill of those in the art. See, for instance, Kim et al., "Effects of Multiple Mutations at the Conserved TATA Sequence of Bacteriophage SP6 Promoter on Transcription Activity", *Biochem. and Mol. Biol. Int.*, 31(1):153–9 (1993), and Pauly, et al., "The Initiation of Accuracy of the SV40 Early Transcription is Determined by the Functional Domains of Two TATA elements", *Nucleic Acids Res.*, 20(5):975–982 (1992).

Pauly et al. further describe a method for the determination of relative and absolute promoter activity levels that is useful in the present invention. In particular, the method of Pauly et al. can be used to compare the activity of mutated promoter regions with their corresponding wild type forms.

A vector falling within the scope of the present invention can be identified by first isolating and identifying the type of promoter used for expressing the marker protein. In turn, those skilled in the art will be able to identify and obtain the corresponding wild type constructs of most, if not all, promoter regions. Having identified and obtained both the promoter used in the vector, and its corresponding wild type (i.e., native) construct, those skilled will then be able to perform a suitable assay, as taught by Pauly et al., to determine their relative activity levels.

In a preferred embodiment, a weakened promoter of the present invention demonstrates activity on the order of 50% or less of its corresponding wild type form, when determined according to the method set forth in Pauly et al. In a preferred embodiment, a mutation is introduced into the marker sequence promoter in order to reduce its transcriptional activity to between about 10% and about 50%, as compared to the native form and more preferably between about 10% and about 20% of that of the native promoter.

If the promoter expression level is lowered too much, as compared to that of the cDNA promoter, there may be too little expression of marker to allow the identification or recovery of transfectants. On the other hand, if the promoter is too strong as compared to the cDNA promoter, it is possible that even a significant inhibition of its activity might still provide enough residual activity to prevent its use in a vector of the present invention.

In a preferred construction, where the gpt system is employed as the marker protein, the corresponding gene is expressed from the SV40 "early" promoter. Many selection markers other than those used to confer antibiotic resistance, such as those relating to biosynthetic pathways, can be used as well.

In its native configuration, the SV40 promoter region provides a single regulatory region serving two different sets of genes, encoded on opposite strands and used early and late in infection, respectively. The main functional elements in the promoter are the TATA box, located 25 base pairs 5' to the start site for the early viral transcripts; a series of six GC boxes organized into three tandem repeats of 21 to 22 base pairs; and an enhancer, tandemly repeated 72 base pair elements. There is no discernable TATA box for the late viral mRNA promoter, however, Japanese Patent Application No. JP 62011096 describes the incorporation of a TATA box domain into the SV40 late gene promoter. As is often the case for a promoter without a TATA box, transcript initiation occurs at many sites for the late viral transcripts.

The invention further provides an expression system comprising a mammalian cell line incorporating an expression vector as described herein, wherein the vector allows the rapid identification and selection of suitable cell lines expressing the cDNA sequence.

Suitable host cells for use in connection with the vector of the present invention include those cell lines capable of incorporating and expressing the structural and marker protein products of the present vector. Examples of suitable host cell lines include mouse myeloma cell lines such as NSO, NS-1, P3-X63Ag8, and Sp2/0-Ag14 cell lines.

The expression vector can be used to transfect cells according to methods known to those skilled in the art. When a vector of the present invention is used to transfect host cells, the successful clones can be identified by the selectable marker. Those demonstrating the presence of the marker can be grown and individually tested for cDNA expression.

In another aspect, the invention provides a method of using a vector of the type described herein, and a corresponding method of using the corresponding expression system. Both methods involve the steps of (a) transfecting a mammalian cell population with a vector of the present invention, and (b) identifying those clones that demonstrate the expression of marker protein in order to identify those clones having the vector integrated into transcriptionally active regions.

The invention will be further described by the following non-limiting examples. Unless otherwise indicated, all percentages are by weight.

EXAMPLE

Example 1

Preparation of Constructs

Constructs incorporating either a wild type or mutagenized SV40 early promoter region were prepared and assayed in the following manner.

To prepare the knockdown construct, the SV40 early promoter region was subjected to site-specific mutagenesis using standard techniques as set forth in the Sambrook and Pauly et al. references (both cited above). The technique involved first sublconing a small region of DNA that included the TATA box, then subjecting the region to site-specific mutagenesis in order to mutate the AT to a CG sequence. The mutated region was sequenced for confirmation and reintroduced into its original site within the construct.

The promoter identified as A-series mutation number 7 in FIG. 3B of Pauly et al. was prepared. In this promoter, the wild type region 5'-TATTTA-3', located at position 16 to 21, has been mutated to corresponding sequence 5'-TCGTTA-3'

As described in Pauly et al., this particular mutation is shown to provide a relative in vivo transcription rate that is 14% that of the wild type (pSEG A0).

An NS0 murine myeloma cell line (Galfre and Milstein, 1981 available from European Collection of Animal Cell Cultures, ECACC #85110503, Portondown, UK) was maintained in Dulbecco's Modified Eagle Medium ("DMEM") which was supplemented with 4.5 mg/l D-glucose, 4 mM L-glutamine, and 10% heat-inactivated fetal bovine serum (Biocell, Rancho Dominguez, Calif.). The supplemented DMEM will be referred to as "HIFBS-DMEM" in the present application. NS0 cells were harvested from an exponentially growing culture, rinsed once in phosphate buffered saline ("PBS", pH 7.3–7.4) and resuspended in PBS on ice at a concentration of $1 \times 10^7$ cells/ml. 40 micrograms of either the wild type or knockdown construct, in the form of supercoiled plasmid DNA, was added to 0.90 ml of an NS0 cell suspension in an electroporation cuvette (BioRad Laboratories, Hercules, Calif.) and incubated on ice for 10 min.

Electroporation was performed with a BioRad Gene Pulser, using two pulses of 1500 V at a resistance of 200 ohms and capacitance of 3.0 microFarads. Following electroporation the cuvette was placed on ice for an additional 10–15 min. The cells were then added to 22 ml of plating media which consisted of a 1:1 mixture of NS0 conditioned media (cell free medium of exponential phase cells) and fresh 10% HIFBS-DMEM (prepared as described above). This cell suspension was diluted 1:10 with additional plating media and both the undiluted and diluted cell suspensions were plated out in 96 well plates (Corning, Corning, N.Y.) using 50 microliter cell suspension per well. After 48 hr of culture (37 degrees C., 5% CO2), 200 microliter gpt selection media was added to each well.

Gpt selection medium was prepared as HIFBS-DMEM medium further supplemented with 250 microgram/ml xanthine, 15 microgram/ml hypoxanthine, 10 microgram/ml thymidine (all Sigma) and 2.5 microgram/ml mycophenolic acid (Life Technologies). After 10–14 days of selection in 37 degrees C. culture, individual clones were expanded into 24 well plates and sequentially into T25 and T75 culture flasks (Corning).

Exponentially growing cells were harvested and plated in 6-well plates at a concentration of $2 \times 10^6$ cells per well in 5 ml fresh gpt selection media. After 7 days of culture the conditioned media was removed for analysis of cDNA protein expression levels.

Example 2

Evaluation of Constructs

The expression of integrated constructs prepared as in Example 1 was determined using two approaches; first, by employing myeloma derived cell lines (NS0 and NS1), and second, using expression vectors having "stronger" promoters. Myeloma derived cell lines are considered attractive candidates for expression studies, since their function is the synthesis and expression of large amounts of proteins.

Expression vectors were constructed as described in Example 1 having the following structures, which differ only in the sequence of the gpt promoter identified as component (8) (5' to 3' reading sequence):

(1) an SRα296 promoter, which is an SV40 early promoter;
(2) an intron;
(3) a multiple cloning site useful for inserting a cDNA of interest;
(4) a cDNA of interest;
(5) a beta globin poly A gene;
(6) the heavy chain enhancer from the IgG gene, to act as a transcriptional enhancer;
(7) a gene conferring ampicillin resistance (AMPr);
(8) gpt SV40 early promoter in the form of a wild type or mutated (A series, No. 7) SV40 early promoter region;
(9) gpt gene as a selectable marker;
(10) SV40 polyA region.

Both wild type and mutant constructs were prepared according to the method of Example 1, incorporating human IL-6 soluble receptor as the cDNA of choice. The resulting constructs were separately transferred into the mouse myeloma cell line, NS0, by electroporation. After outgrowth to allow for gpt expression, at 37C as in Example 1, 120 individual clones were isolated by selection for xanthine utilization in the presence of mycophenolic acid. Each separate clone represented an independent integration event of the expression construct into the host genome. The integration sites were considered to be essentially random. After the isolation of individual clones, they were grown up in gpt expression medium for 7 days. This medium wits then screened for cDNA (hIL-6 receptor) expression levels. The results are depicted in TABLE 1 below.

TABLE 1

| Activity | (number of clones) | |
| --- | --- | --- |
| (ng/ml) | Wild type | Knockdown |
| 0–100 | 4 | 6 |
| 100–1000 | 3 | 6 |
| 1000–5000 | 17 | 2 |
| 5000–20000 | 12 | 24 |
| >20000 | 1 | 7 |

As can be seen in TABLE 1, the presence of the knockdown mutation led to a greater number of clones providing cDNA expression of over 5000 ng/ml, as compared to the wild type construct. Furthermore, seven of the knockdown clones provided expression of >20,000 ng/ml, as compared to only one of the wild type. This approximate ratio of knockdown to wild type clones exhibiting >20,000 ng/ml has been confirmed in repeated experiments of the same sort.

Since the integration into the host genome for the establishment of stable cell lines was apparently random, the expression levels of otherwise identical constructs was found to vary dramatically. It follows that integration into a transcriptionally active "hot spot" area of the chromosome leads to high expression of the linked cDNA insert while integration into a transcriptionally quiet area of the chromosome leads to relatively low levels of expression. The experiment described in this Example was useful for identifying and distinguishing desired clones with insertions into transcriptionally active "hot spots".

Since mycophenolic acid inhibition of IMP dehydrogenase leads to GMP starvation, growth on xanthine was the limiting factor for cell growth in the gpt selection. Because xanthine is a relatively poor substrate for gpt, the NS0 cells have a need for relatively high levels of gpt expression. It was found that by lowering the expression of gpt, the NS0 cell line could be made more dependent on the level of gpt expression. In turn, it was possible to eliminate those clones where the expression constructs had integrated into a poorly transcribed region of the host genome.

What is claimed is:

1. A vector useful for selection and expression of a cDNA gene sequence in a mammalian system, the vector comprising;

a) a cDNA structural gene sequence encoding a protein product of choice;

b) a cDNA promoter sequence controlling the cDNA sequence;

c) a native marker protein sequence encoding a detectable protein product; and d) a marker promoter sequence controlling the marker protein sequence;

wherein the cDNA structural gene and marker promoter sequences are cotransformed, and the marker sequence promoter is mutated so as to exhibit an activity level substantially below that of its corresponding wild type.

2. A vector according to claim 1 wherein the marker sequence promoter is an SV40 early promoter that has been stably, genetically mutated from its corresponding wild type.

3. A vector according to claim 2 wherein the marker protein sequence encodes a mycophenolic/gpt selection system.

4. A vector according to claim 2 wherein the marker sequence promoter is selected frown the group consisting of double and single transvertional point mutations covering the T+A rich region of the SV 40 early promoter and replication origin.

5. A vector according to claim 4 wherein the promoter has been mutated by a mutation located within the TATTTA wild type region.

6. A vector according to claim 2 wherein the SV40 promoter wild type is SEG A0.

7. An expression system comprising a mammalian cell line incorporating a vector according to claim 1.

8. An expression system according to claim 7 wherein the marker protein sequence encodes a mycophenolic/gpt selection system, the marker protein promoter is a mutated SV40 early promoter, and the cell line is a NSO mouse myeloma cell line.

9. An expression system according to claim 8 wherein the marker sequence promoter is selected from the group consisting of double and single transvertional point mutations covering the T+A rich region of the SV 40 early promoter and replication origin.

10. An expression system according to claim 9 wherein the promoter has been mutated by a mutation is located within the TATTTA wild type region.

11. An expression system according to claim 9 wherein the SV40 promoter wild type is SEG A0.

12. A method of making a vector useful for selection and expression of a cDNA gene sequence in a mammalian system, the method comprising the steps of providing a) a cDNA structural gene sequence encoding a protein product of choice;

b) a cDNA promoter sequence controlling the cDNA structural gene sequence;

c) a native marker protein sequence encoding a detectable protein product; and d) a marker promoter sequence controlling the marker protein sequence; and using each sequence to construct a vector wherein the cDNA structural gene and marker promoter sequences are cotransformed, and the marker sequence promoter is mutated so as to exhibit an activity level substantially below that of its corresponding wild type.

13. A method of using a vector for the selection and expression of a cDNA gene sequence in a mammalian system, the method comprising the steps of (a) transfecting a mammalian cell population with a vector according to claim 1 and growing the transfected cells to produce individual clones, and (b) identifying clones that demonstrate expression of marker protein in order to identify clones having the vector integrated into a transcriptionally active region.

14. A method according to claim 12 wherein the marker sequence promoter is an SV40 early promoter that has been stably, genetically mutated from its corresponding wild type.

15. A method according to claim 12 wherein the marker protein sequence encodes a mycophenolic/gpt selection system.

16. A method according to claim 14 wherein the marker sequence promoter is selected from the group consisting of double and single transvertional point mutations covering the T+A rich region of the SV 40 early promoter and replication origin.

17. A method according to claim 16 wherein the promoter has been mutated by a mutation located within the TATTTA wild type region.

18. A method according to claim 14 wherein the SV40 promoter wild type is SEG A0.

19. A method according to claim 12 wherein the marker protein sequence encodes a mycophenolic/gpt selection system, the marker protein promoter is a mutated SV40 early promoter, and the vector is expressed in an NSO mouse myeloma cell line.

20. A method according to claim 19 wherein the marker sequence promoter is selected from the group consisting of double and single transvertional point mutations covering the T+A rich region of the SV 40 early promoter and replication origin.

21. A method according to claim 20 wherein the promoter has been mutated by a mutation located within the TATTTA wild type region.

22. A method according to claim 13 wherein the marker sequence promoter is an SV40 early promoter that has been stably, genetically mutated from its corresponding wild type.

23. A method according to claim 13 wherein the marker protein sequence encodes a mycophenolic/gpt selection system.

24. A method according to claim 22 wherein the marker sequence promoter is selected from the group consisting of double and single transvertional point mutations coveting the T+A rich region of the SV 40 early promoter and replication origin.

25. A method according to claim 22 wherein the promoter has been mutated by a mutation located within the TATTTA wild type region.

26. A method according to claim 13 wherein the SV40 promoter wild type is SEG A0.

27. A method according to claim 13 wherein the marker protein sequence encodes a mycophenolic/gpt selection system, the marker protein promoter is a mutated SV40 early promoter, and the vector is expressed in an NSO mouse myeloma cell line.

28. A method according to claim 27 wherein the marker sequence promoter is selected from the group consisting of double and single transvertional point mutations covering the T+A rich region of the SV 40 early promoter and replication origin.

29. A method according to claim 28 wherein the promoter has been mutated by a mutation located within the TATTTA wild type region.

* * * * *